US012806015B2

(12) United States Patent
Zarbatany et al.

(10) Patent No.: US 12,806,015 B2
(45) Date of Patent: Nov. 24, 2026

(54) EDGE TO EDGE REPAIR OF THE MITRAL VALVE

(71) Applicant: Ventrimend, Inc, Lake Forest, CA (US)

(72) Inventors: David Zarbatany, Lake Forest, CA (US); Ricardo Roman, Lake Forest, CA (US); Jesus Flores, Lake Forest, CA (US)

(73) Assignee: VENTRIMEND, INC, Lake Forfeit, CA (US)

(*) Notice: Subject to any disclaimer, the term of this patent is extended or adjusted under 35 U.S.C. 154(b) by 1058 days.

(21) Appl. No.: 17/887,475

(22) Filed: Aug. 14, 2022

(65) Prior Publication Data

US 2023/0048179 A1 Feb. 16, 2023

Related U.S. Application Data

(60) Provisional application No. 63/233,138, filed on Aug. 13, 2021.

(51) Int. Cl.

| | |
|---|---|
| ***A61F 2/24*** | (2006.01) |
| ***A61B 17/00*** | (2006.01) |
| ***A61B 17/04*** | (2006.01) |

(52) U.S. Cl.

CPC ............ *A61F 2/246* (2013.01); *A61F 2/2463* (2013.01); *A61F 2/2466* (2013.01); *A61B 2017/00247* (2013.01); *A61B 2017/0409* (2013.01); *A61B 17/0469* (2013.01); *A61F 2220/0075* (2013.01)

(58) Field of Classification Search

CPC ...... A61F 2/246; A61F 2/2463; A61F 2/2466; A61F 2220/0075; A61B 17/0469; A61B 2017/00247; A61B 2017/0409; A61B 17/0487; A61B 2017/00243; A61B 2017/00292; A61B 2017/00358; A61B 2017/00783; A61B 2017/0417; A61B 2017/0488; A61B 2017/0496; A61B 2017/06052; A61B 17/0401

See application file for complete search history.

(56) References Cited

U.S. PATENT DOCUMENTS

| | | | | |
|---|---|---|---|---|
| 6,086,608 A * | 7/2000 | Ek | ...................... | A61B 17/0487 606/301 |
| 8,382,829 B1 * | 2/2013 | Call | ...................... | A61F 2/2466 623/2.37 |
| 2004/0098050 A1 | 5/2004 | Foerster | | |
| 2007/0005081 A1 | 1/2007 | Findlay, III et al. | | |
| 2018/0221016 A1 * | 8/2018 | Conklin | ............. | A61B 17/0401 |
| 2019/0000624 A1 | 1/2019 | Wilson | | |

(Continued)

FOREIGN PATENT DOCUMENTS

WO WO-2020187944 A1 * 9/2020 ........... A61F 2/2457

OTHER PUBLICATIONS

International Search Report and Written Opinion in PCT Application No. PCT/US22/40278 dated Nov. 17, 2022.

*Primary Examiner* — Sarah W Aleman
*Assistant Examiner* — Rachel S Highland
(74) *Attorney, Agent, or Firm* — Michael R. Shevlin

(57) ABSTRACT

The present invention describes systems and methods for treating mitral valve regurgitation. The treatment includes a systems and method of modifying the mitral valve by attaching a device to each leaflet and pulling them toward each other to stop mitral valve regurgitation.

17 Claims, 12 Drawing Sheets

(56) References Cited

U.S. PATENT DOCUMENTS

| | | | |
|---|---|---|---|
| 2019/0133575 | A1 | 5/2019 | Maisano et al. |
| 2020/0281582 | A1 | 9/2020 | Caffes et al. |
| 2021/0038387 | A1 | 2/2021 | Zhang et al. |

* cited by examiner

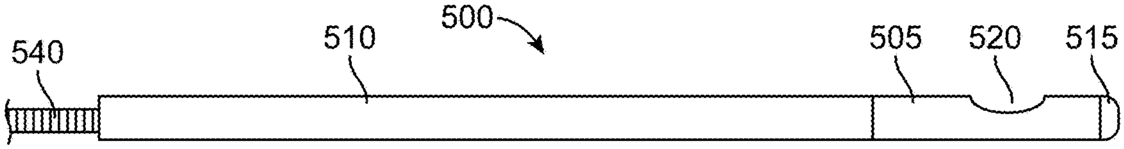
FIG. 24
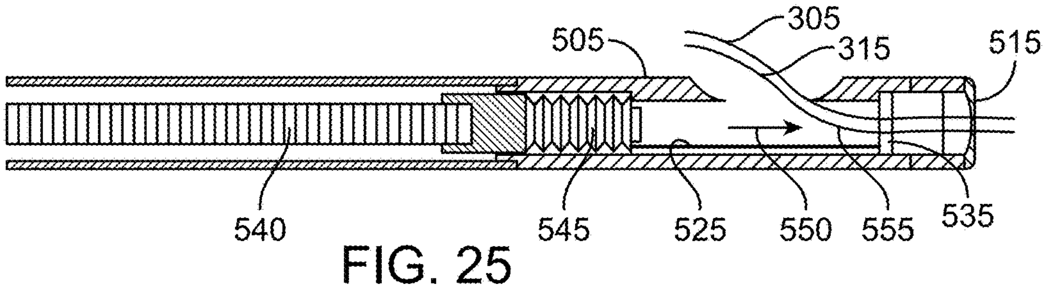
FIG. 25
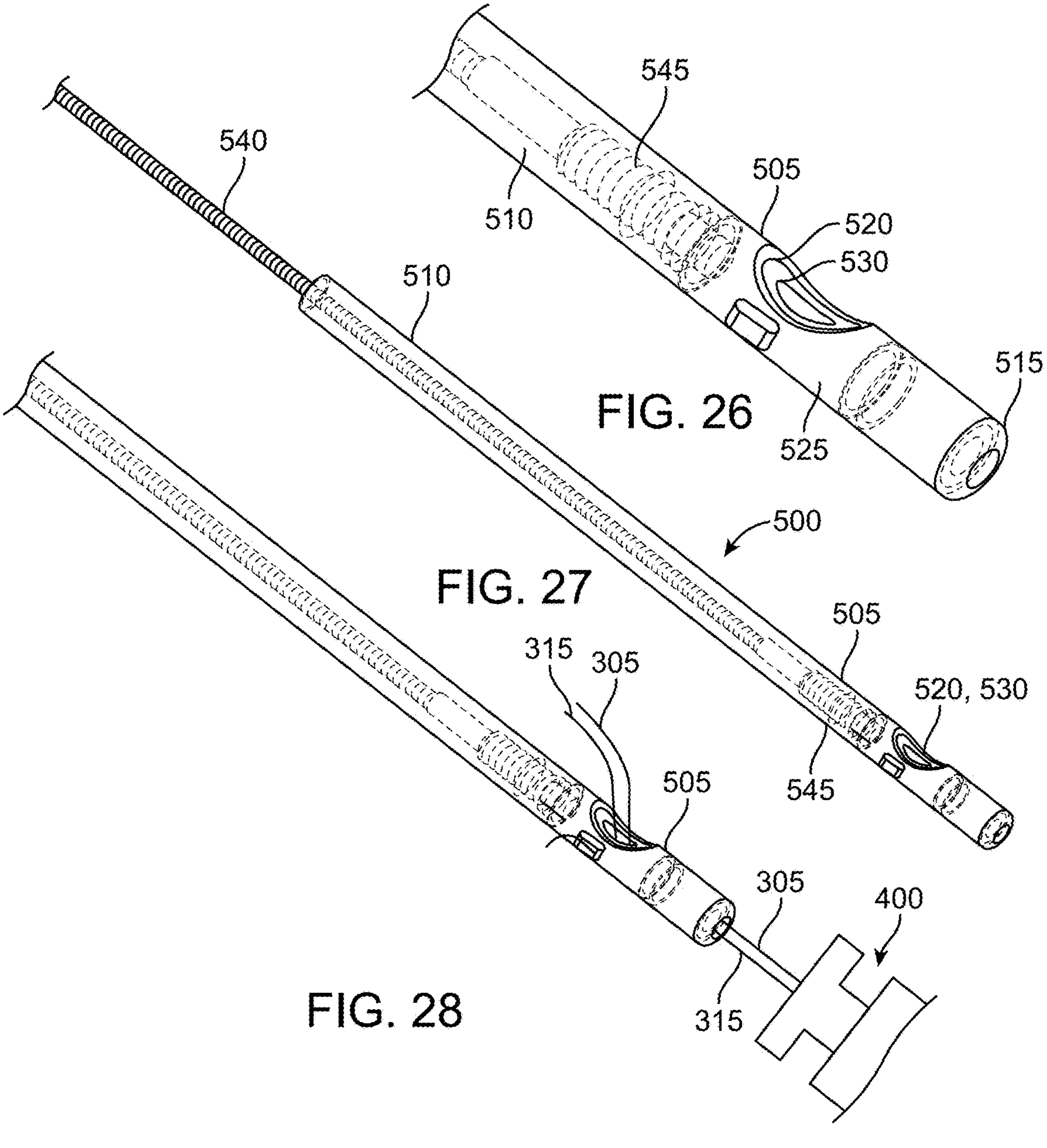
FIG. 26
FIG. 27
FIG. 28

EDGE TO EDGE REPAIR OF THE MITRAL VALVE

CROSS-REFERENCE TO RELATED APPLICATIONS

This application claims priority to U.S. Provisional Patent Application No. 63/233,138, filed Aug. 13, 2021, the entire disclosure of which is incorporated by reference herein.

FIELD

The present invention relates generally to the field of surgery, and more specifically, to repair of a mitral valve.

BACKGROUND

The heart has four valves that keep blood flowing in the correct direction. The valves include the mitral valve, tricuspid valve, pulmonary valve and aortic valve. Each valve has flaps (leaflets or cusps) that open and close once during each heartbeat. Sometimes, the valves don't open or close properly, disrupting the blood flow through your heart to your body.

The mitral valve lies between the left atrium and the left ventricle. Normally, the mitral valve prevents blood flowing back into the left atrium from the left ventricle. When the mitral valve becomes leaky, it's called mitral valve regurgitation. Mitral valve regurgitation is a condition in which the mitral valve leaflets do not close tightly, allowing blood to flow backward through the mitral valve each time the left ventricle contracts. A leaking mitral valve allows blood to flow in two directions during the contraction. Some blood flows from the ventricle through the aortic valve and some blood flows back into the atrium. Leakage can increase blood volume and pressure in the left atrium. The increased pressure can increase pressure in the veins leading from the lungs to the heart (pulmonary veins). If regurgitation is severe, increased pressure may result in congestion (or fluid build-up) in the lungs. Because of this, the heart has to work harder than it should to get blood out to the body.

Accordingly, there is a need for systems and methods that provide solutions to repair mitral valve regurgitation. The present invention is directed toward systems and methods for treating these problems.

SUMMARY

The present invention describes systems and methods for treating mitral valve regurgitation. The treatment includes a systems and method of modifying the mitral valve by attaching a device to each leaflet and pulling them toward each other to stop mitral valve regurgitation.

BRIEF DESCRIPTION OF THE DRAWINGS

FIGS. 24-28 are views showing the cutter.

DETAILED DESCRIPTION

The present invention describes systems and methods for treating mitral valve regurgitation. The treatment includes a systems and method of modifying the mitral valve by attaching a device to each leaflet and pulling them toward each other to stop mitral valve regurgitation.

A therapy catheter initially grasps the leaflets and a therapy catheter needle is used to puncture through the leaflets. A therapy catheter is used to deliver leaflet anchors with tethers to the leaflets. The leaflet anchors are then attached to the leaflets and pulls the leaflets toward each other. The leaflets are fixed in the desired position.

The steps include a therapy catheter directed to a first mitral valve leaflet. Through a double steerable sheath system. The “outer sheath”/transseptal sheath is placed across the intra-atrial septum from the RA to the LA. The “inner steerable”/guiding catheter is placed through the outer sheath and deflected to set a trajectory to the target location for the leaflet anchor.

The therapy catheter, internal to the inner steerable, depth is adjusted and the first leaflet is grasped.

The therapy catheter includes a cannulated needle used to puncture the first leaflet.

A first leaflet anchor and first tether are then delivered through the cannulated needle to the distal/LV side of the first leaflet. The first anchor then expands and contacts the distal/LV side of the first leaflet. The first tether is exposed as the catheter is removed.

A second leaflet anchor is delivered to the second leaflet. The second tether is exposed.

The first and second tethers are expose through the outer steerable catheter at the groin are inserted into the “knot replacement” tool.

The knot replacement is positioned at the leaflet, the tethers are tensioned, and the knot replacement is engaged and released, leaving the tethers exposed at the groin.

The Tether Cutting Catheter follows the tethers to the knot replacement tool and are cut.

The therapy catheter initially grasps the leaflets and a therapy catheter needle is used to puncture through the leaflet. A therapy catheter is used to deliver leaflet anchors (buttons) with tethers to the leaflets. The leaflet anchors are then attached to the leaflets and pulls the leaflets toward each other, creating a coaptation area for the 2 leaflets. Once the leaflets are in the desired position. The is directed to the leaflet anchor (button) targeted location.

The Therapy Catheter depth is adjusted and the leaflet is grasped.

The Therapy Catheter needle is punctured through the leaflet to the Left Ventricle side of the leaflet.

The leaflet button is delivery and the tether is exposed as the Catheter is removed.

An opposing leaflet anchor is delivery and the tether is exposed.

The two exposed tethers exiting from the groin sheath are inserted into the “knot replacement” tool.

Figure 1:
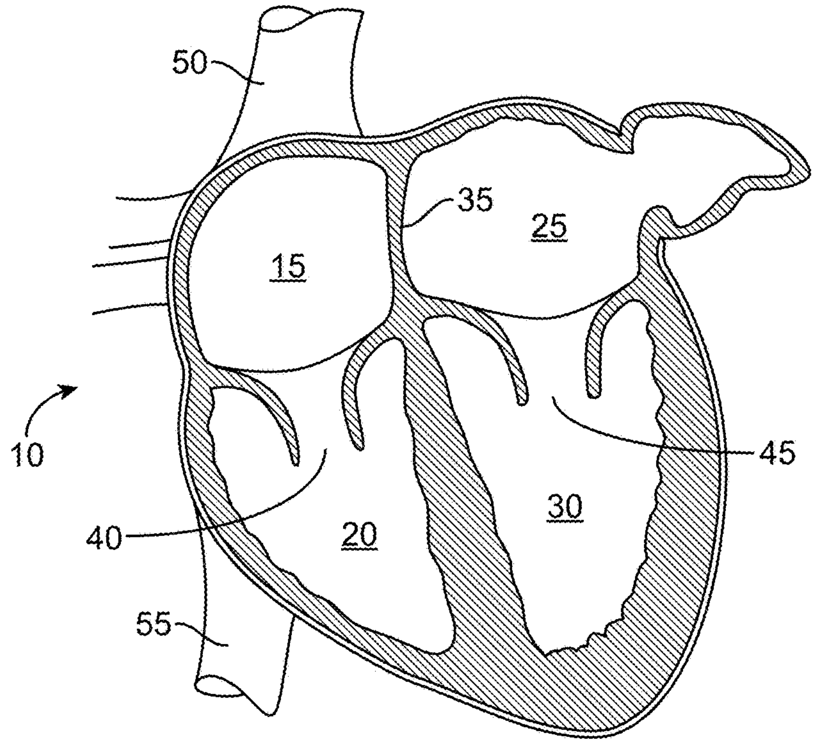
FIG. 1 is a sectional view of the heart anatomy.

The knot replacement is positioned at the leaflet, the tethers are tensioned, and the knot replacement is engaged and released The Tether Cutting Catheter follows the tethers to the knot replacement tool and are cut FIG. 1 is a sectional view of a normal heart anatomy 10. The heart includes four chambers, including a right atrium 15, a right ventricle 20, a left atrium 25 and a left ventricle 30. The right atrium 15 and left atrium 25 are separated by the atrial septum 35. A tricuspid valve 40 allows one way blood to flow from the right atrium 15 into the right ventricle 20. A mitral valve 45 allows one way blood to flow from the left atrium 25 into the left vertical 30.

Blood enters the right atrium 15 from the superior vena cava 50 and the inferior vena cava 55 blood vessels. The blood flows into the right atrium 15, through the tricuspid valve 40 into the right ventricle 20. Blood then flows from the right ventricle 20 into the pulmonary arteries to the lungs. Once through the lungs, the blood flows through the pulmonary veins back to the heart and into the left atrium 25. The blood from the left atrium 25 flows through the mitral valve 45 into the left ventricle 30 and out of the heart through the aortic valve to the ascending aorta.

Figure 2:
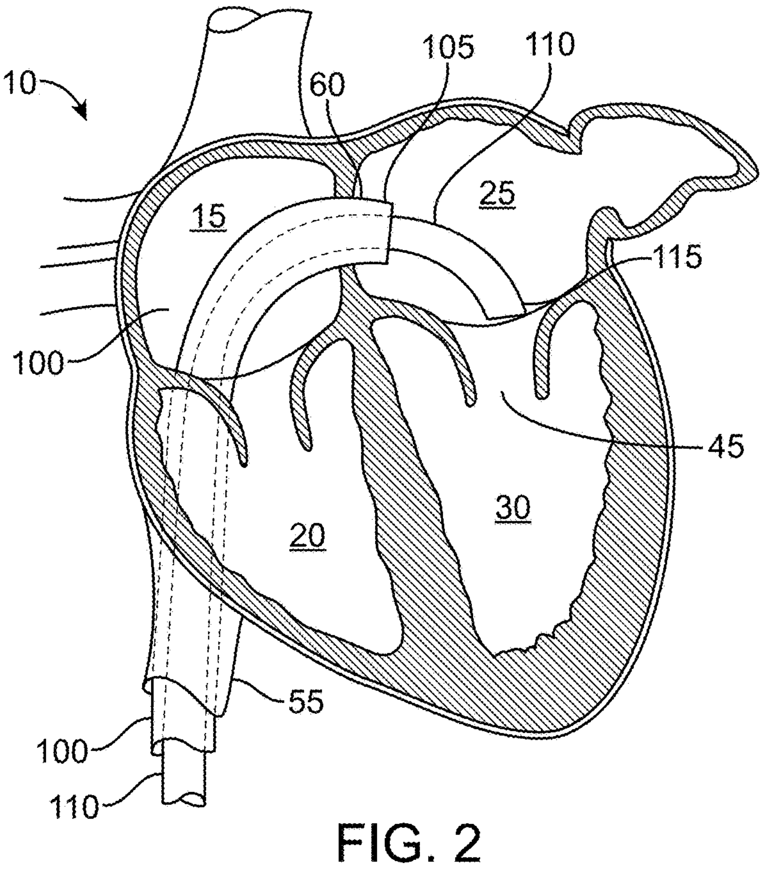
FIGS. 2-11 are sectional view showing the different steps and tool to repair that mitral valve leaflets.

FIG. 2 shows delivery of a delivery system 100, such as an outer steerable/transseptal sheath, that is advanced through the vascular system and into the heart 10 to the LA. The delivery system 100 enters in the femoral vein and is advanced through the vascular system to the heart and into the right atrium 15. The delivery system 100 then goes through the atrial septum 35 to left atrium 25. This can be done by puncturing a hole 60 in the wall of the atrial septum 35 between the right atrium 15 and the left atrium 25, or through a hole 60 of a patent foramen ovale or atrial septal defect, if present. A second steerable sheath 110, such as an inner steerable/guide, is inserted through the delivery system 100 and exits the distal end 105 in the LA. The second steerable sheath 110 then sets the trajectory toward the mitral valve 45. Once in the left atrium 25, the distal end 115 of the second steerable sheath 110 is advanced to the mitral valve 45.

Figure 3:
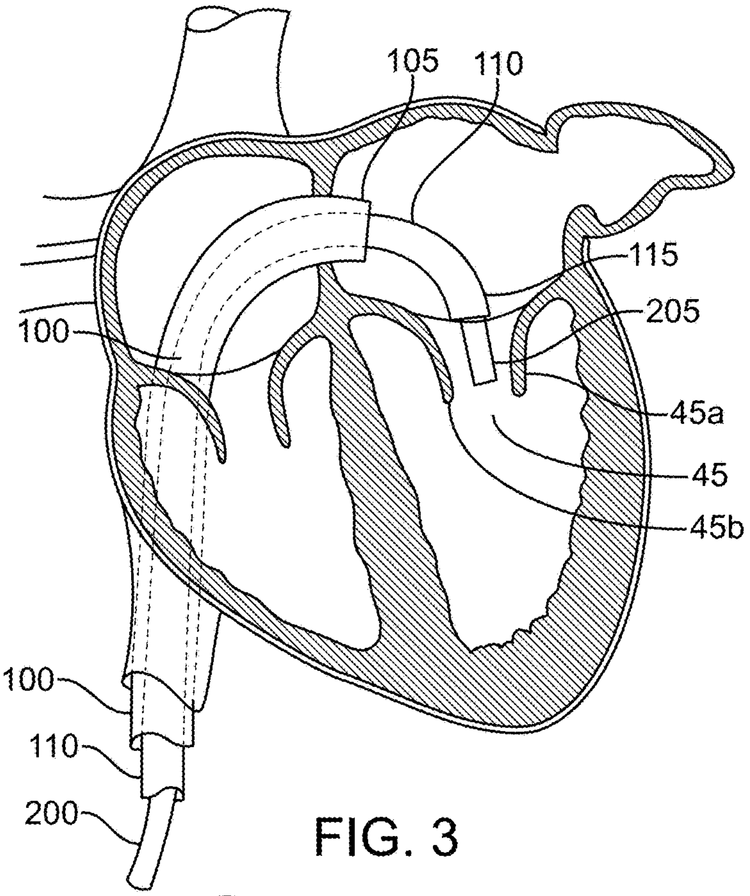

FIG. 3 shows an Inner steerable guide catheter 200 that may have an integrated therapy catheter 205 advanced through a lumen in the Guide Catheter 100. The integrated therapy catheter 205 exits the distal end 105 of the lumen.

Figure 4:
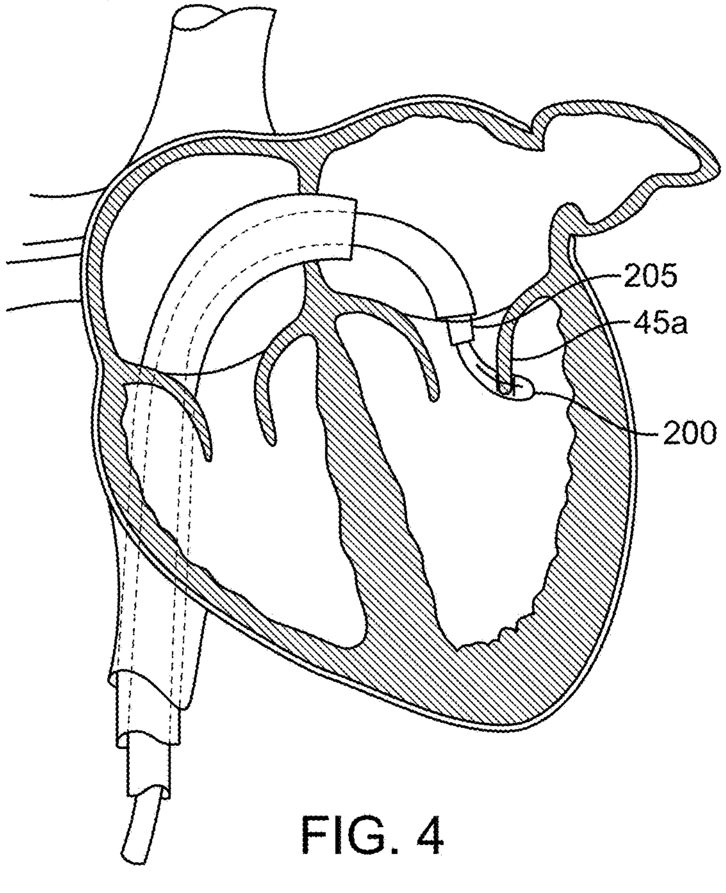

FIG. 4 shows the integrated therapy catheter 205 advanced through the mitral valve 45 into the left ventricle 30. The integrated therapy catheter 200 depth is adjusted and a first leaflet 45*a* is grasped, such as the leaflet to the left ventricle (LV) side. Once grasped, a needle 220 within the integrated therapy catheter 205 advances distally and punctures the first leaflet 45*a*.

The needle 220 is advanced through the leaflet and the integrated therapy catheter 205 then delivers a first leaflet anchor 300 having an attached tether 305 through the puncture in the first leaflet 45*a*. The first leaflet anchor 300 expands or unfolds and contacts a distal side of the first leaflet 45*a*.

Figure 5:
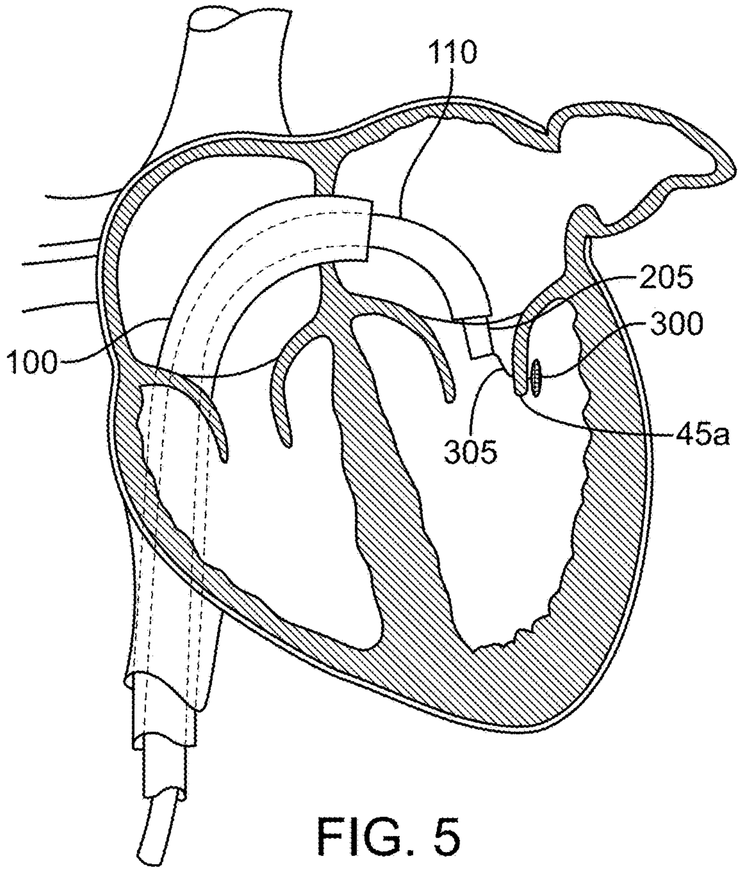

After the first leaflet anchor 300 is secured, the integrated therapy catheter 205 is withdrawn from the first leaflet 45*a*, shown in FIG. 5, exposing the first tether 305 attached to the first anchor 300.

Figure 6:
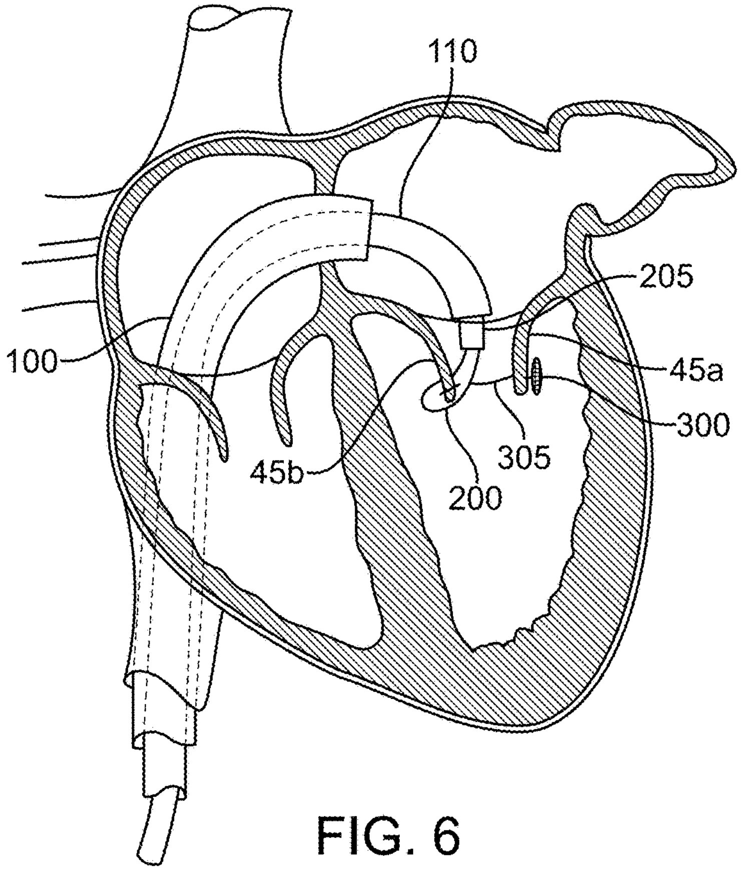

FIG. 6 shows the integrated therapy catheter 205 advanced to the opposite second leaflet 45*b* and the depth is adjusted and the second leaflet 45*b* is grasped. Once grasped, the needle 220 within the integrated therapy catheter 205 advances distally and punctures the second leaflet 45*b*.

The integrated therapy catheter 205 then delivers a second leaflet anchor 310 having a second tether 315 through the puncture in the second leaflet 45*b*. The second leaflet anchor 310 is expanded or unfolds and contacts the distal side of the second leaflet 45*b*.

Figure 7:
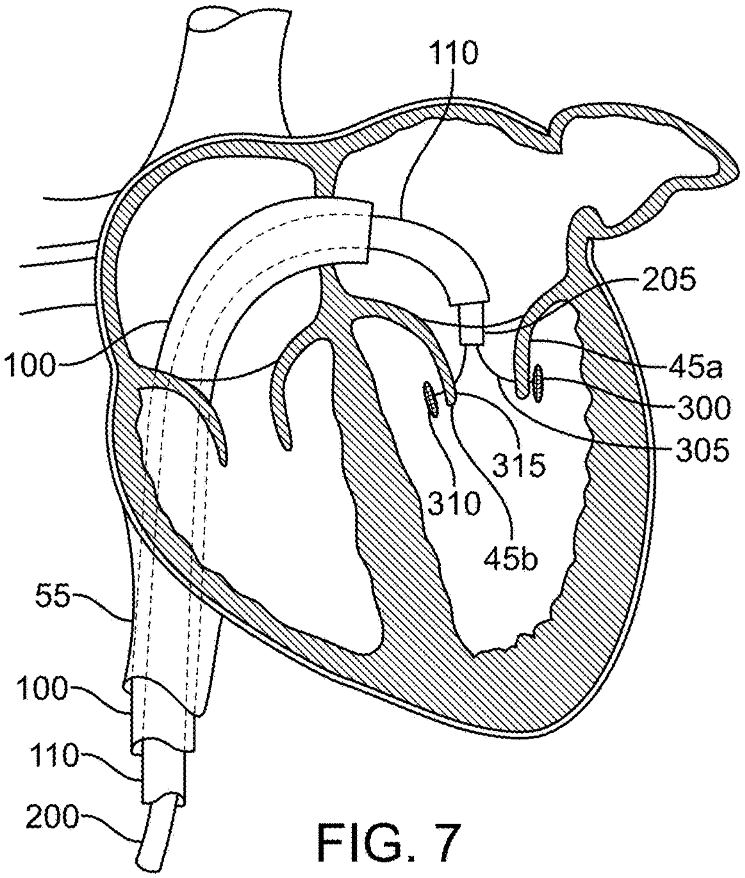

After the second anchor 310 is secured, the integrated therapy catheter 205 is withdrawn from the second leaflet 45*b*, shown in FIG. 7, exposing the second tether 315 attached to the second anchor 310.

Figure 8:
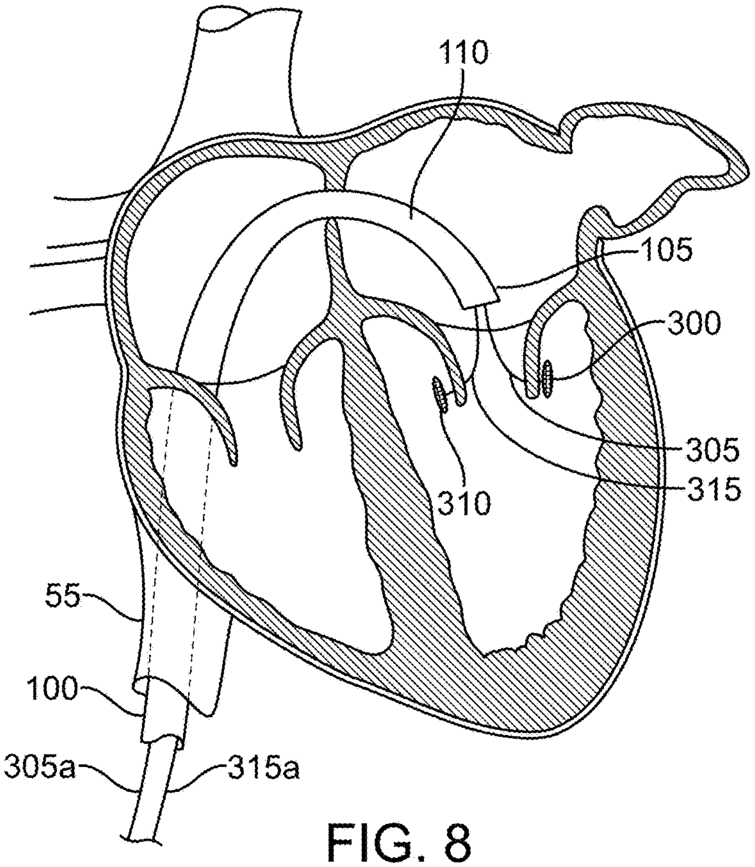

The integrated therapy catheter 205 is then withdrawn from the lumen of the outer steerable catheter 100. After withdrawal, the proximal ends of first and second tethers 305*a*, 315*a* extend from the proximal end 110 of the lumen of the outer steerable catheter 100, shown in FIG. 8.

Figure 9:
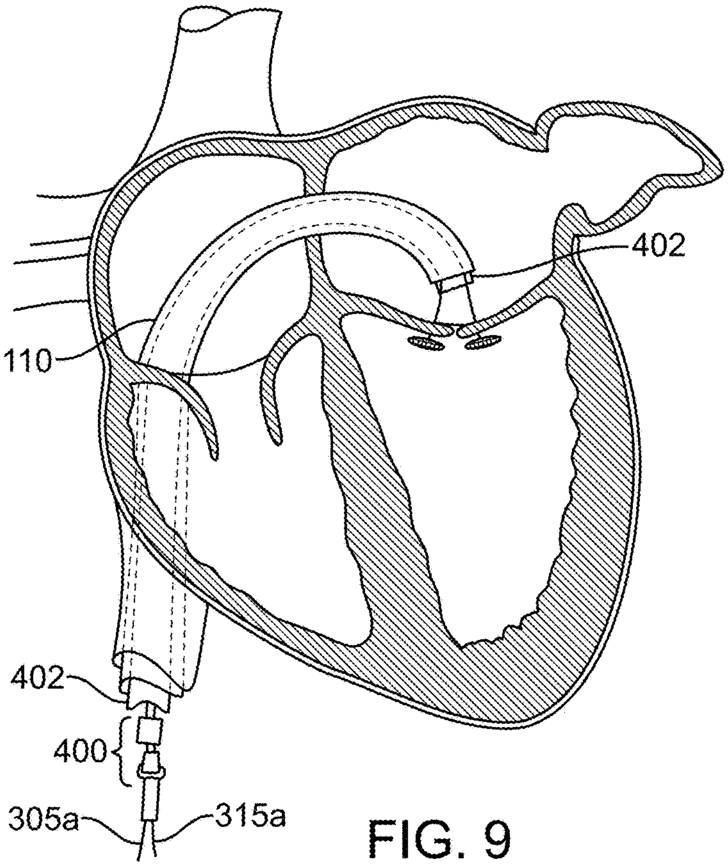

FIG. 9 shows the proximal end of the first and second tethers 305*a*, 315*a* inserted into a "knot replacement" tool 400. A knot replacement delivery catheter 402 is then inserted into the lumen of the Outer Steerable Catheter 100 and uses the first and second tethers 305, 315 as a "rail" to guide it to the mitral valve 45.

Figure 10:
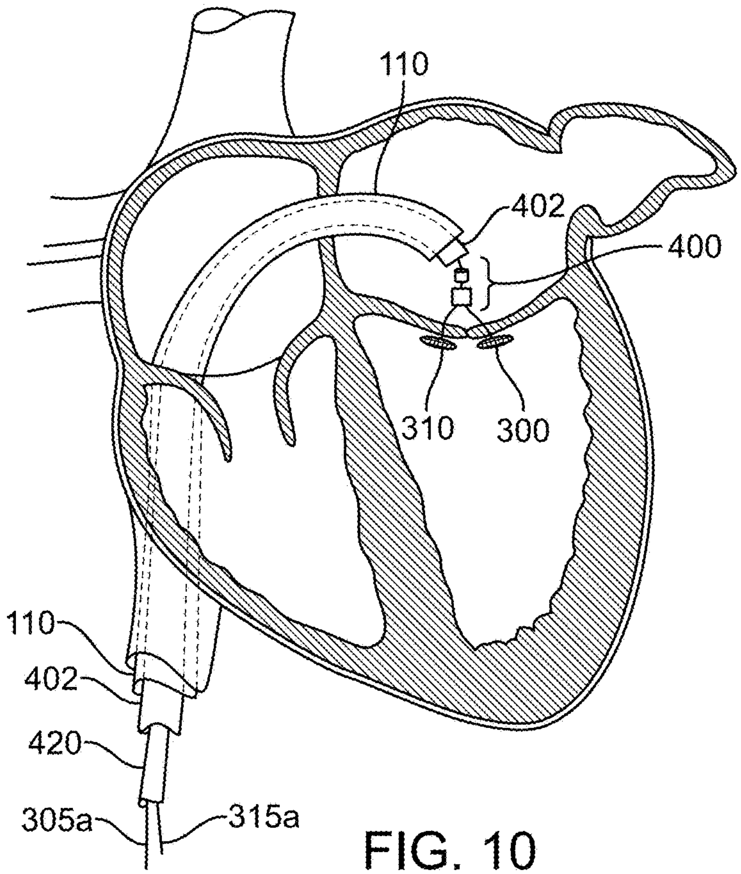

FIG. 10 shows the knot replacement tool 400 in the desired position and the tethers first and second tethers 305, 315 are tensioned so that the edges of the first and second leaflets 45*a*, 45*b* are brought together for coaptation. The knot replacement tool 400 then ties the first and second tethers 305, 315, locking them in place. The knot replacement delivery shaft 420 is detached from the knot replacement tool 400 and then withdrawn from the lumen of the outer steerable catheter 100.

Figure 11:
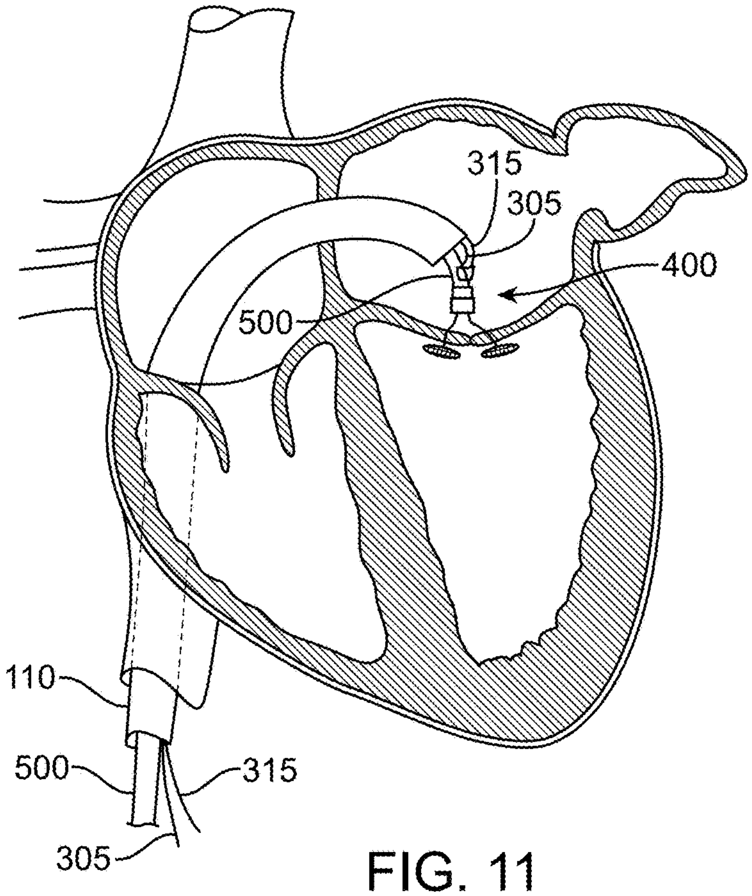

FIG. 11 the proximal end of the first and second tethers 305, 315 inserted into a tether cutter 500. A cutter delivery catheter 502 is inserted into the lumen of the outer steerable catheter 100. The cutter delivery catheter 502 and cutter 500 follow the first and second tethers 305, 315 to the locking cap 505 and locking screw 510. The cutter 500 then cuts the first and second tethers 505, 515 and the cutter delivery catheter 502 withdrawn from the guide catheter 100.

The outer steerable catheter 100 is then withdrawn from the body. If a hole in the septum needs to be repaired, an ASD closure device may be used to close the hole.

Figure 12:
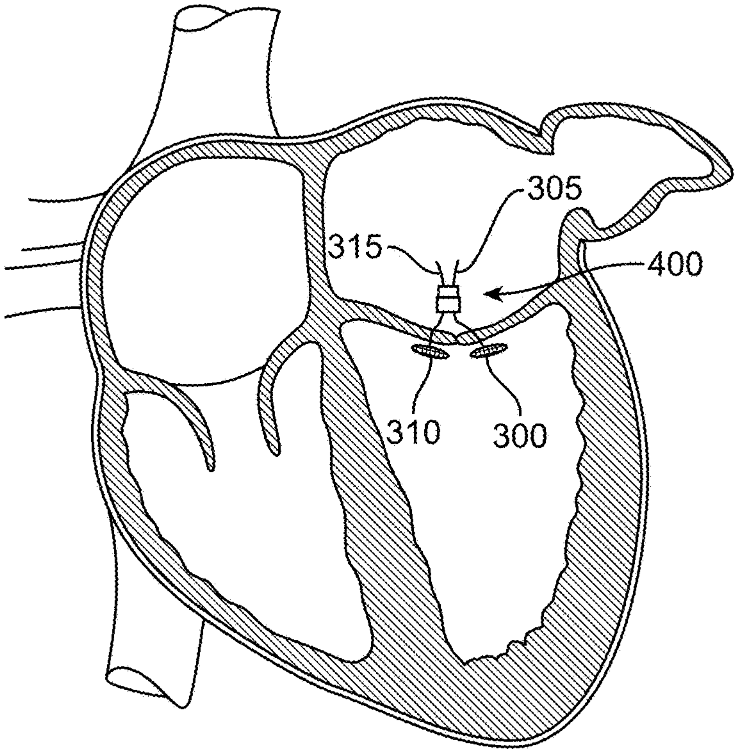
FIG. 12 is a view of a repaired mitral valve.
Figure 13:
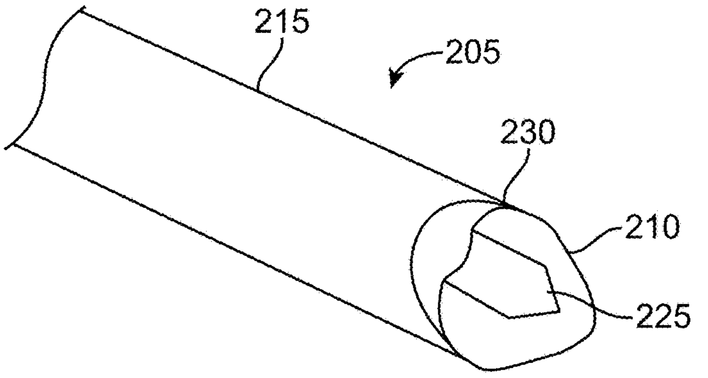
FIGS. 13-16 show a perspective view and side views of an integrated therapy catheter configured to: clamp a leaflet, puncture the leaflet, and deliver one or more leaflet anchors to the leaflet.
Figure 14:
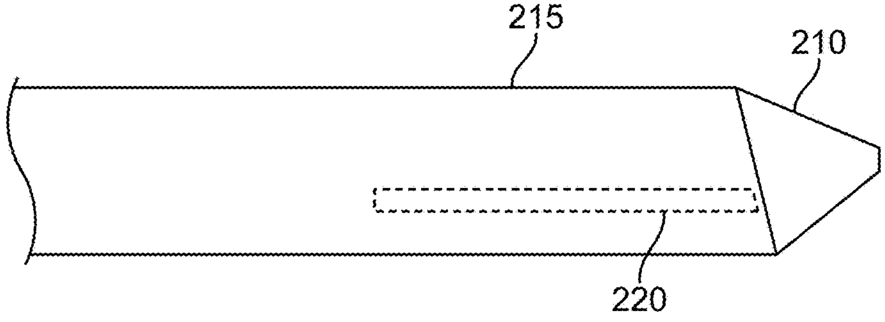
Figure 15:
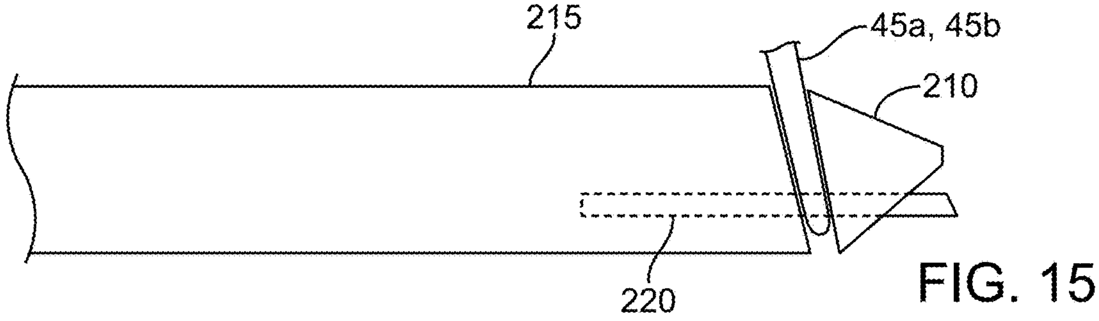
Figure 16:
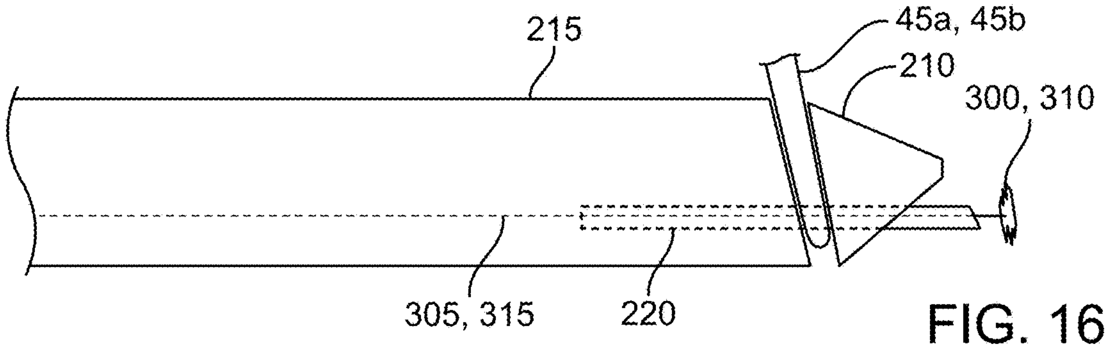

FIG. 12 shows the repaired mitral valve 45 with the first and second leaflets 45*a*, 45*b* closed with the first and second anchors.

Integrated Therapy Catheter

FIGS. 13-16 show a perspective view and side views of an integrated therapy catheter 205 configured to: clamp a leaflet, puncture the leaflet, and deliver one or more leaflet anchors to the leaflet. The integrated therapy catheter 205 includes a distal clamp portion 210 slidably coupled to the proximal body portion 215. The distal clamp portion 210 is configured to slide distally, and the leaflet 45*a*, 45*b* is positioned between the distal clamp portion 210 and the proximal body portion 215. The distal clamp portion 210 then moves proximally and the leaflet 45*a*, 45*b* engages distal and proximal clamp surfaces and is clamped between them.

A cannulated needle 220 is positioned within the proximal body portion 215 is configured to extend distally through a needle lumen 225 in the distal clamp portion 210.

Once the leaflet 45*a*, 45*b* is punctured, a leaflet anchor 300, 310 with a tether 305, 315 is delivered through the cannulated needle 220 to the distal side of the leaflet 45*a*, 45*b*. The cannulated needle 220 is then withdrawn and the distal clamp portion 210 extends distally to release the leaflet 45*a*, 45*b*. As then integrated therapy catheter 205 is removed in a downward direction and the tether moves up through the tether slot 230 and the leaflet anchor 300, 310 and tether 305, 315 stays attached to the leaflet 45*a*, 45*b*.

The leaflet anchor self-expands to a size larger than the puncture and engages the distal side of the leaflet. The tether extends proximally through the puncture and out of the body to be grasped during the procedure.

Figure 17:
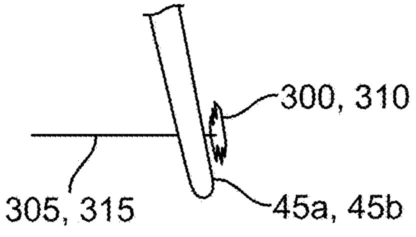
FIG. 17 shows an anchor and tether coupled with a leaflet.

FIG. 17 shows the anchor 300, 310 and tether 305, 315 coupled with the leaflet 45*a*, 45*b*.

"Knot Replacement" Tool

FIGS. 18-21 are views showing one embodiment of a "knot replacement" tool 400 that is configured to couple with the first and second exposed tethers 305, 315 outside the body. The first and second tethers 305, 315 are used as a "rail" to guide the "knot" replacement tool 400 to the targeted location at the first and second leaflets 45*a*, 45*b*.

Figure 18:
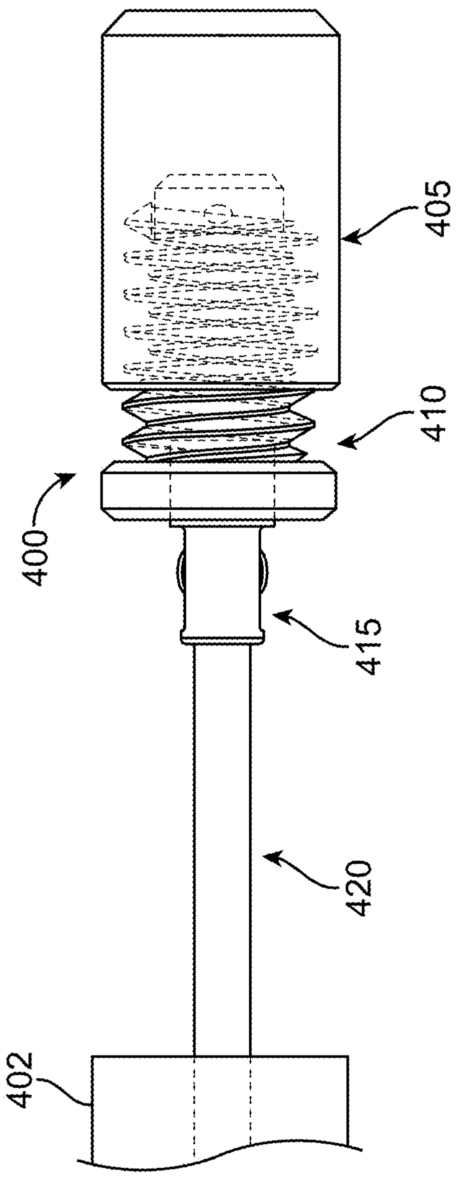
FIGS. 18-21 are views showing one embodiment of a “knot replacement” tool.
Figure 19:
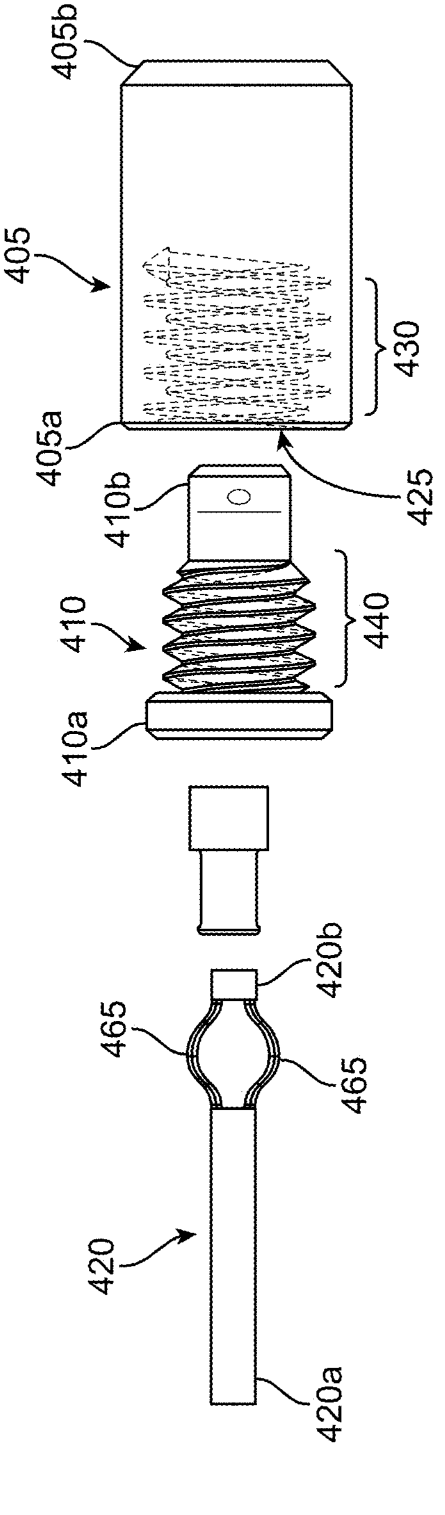
Figure 20:
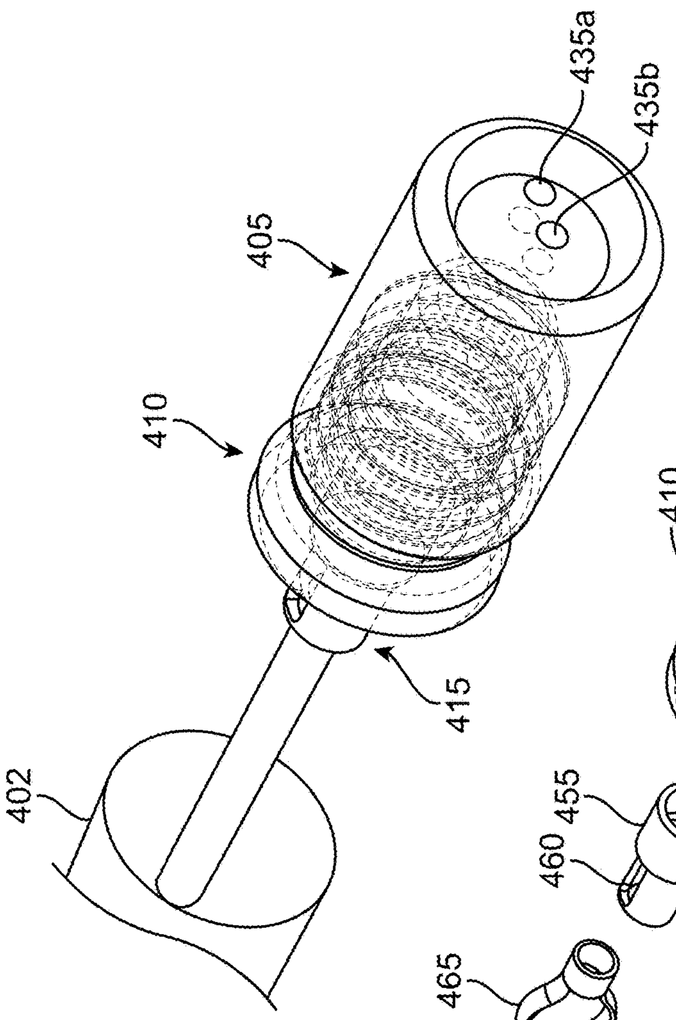
Figure 21:
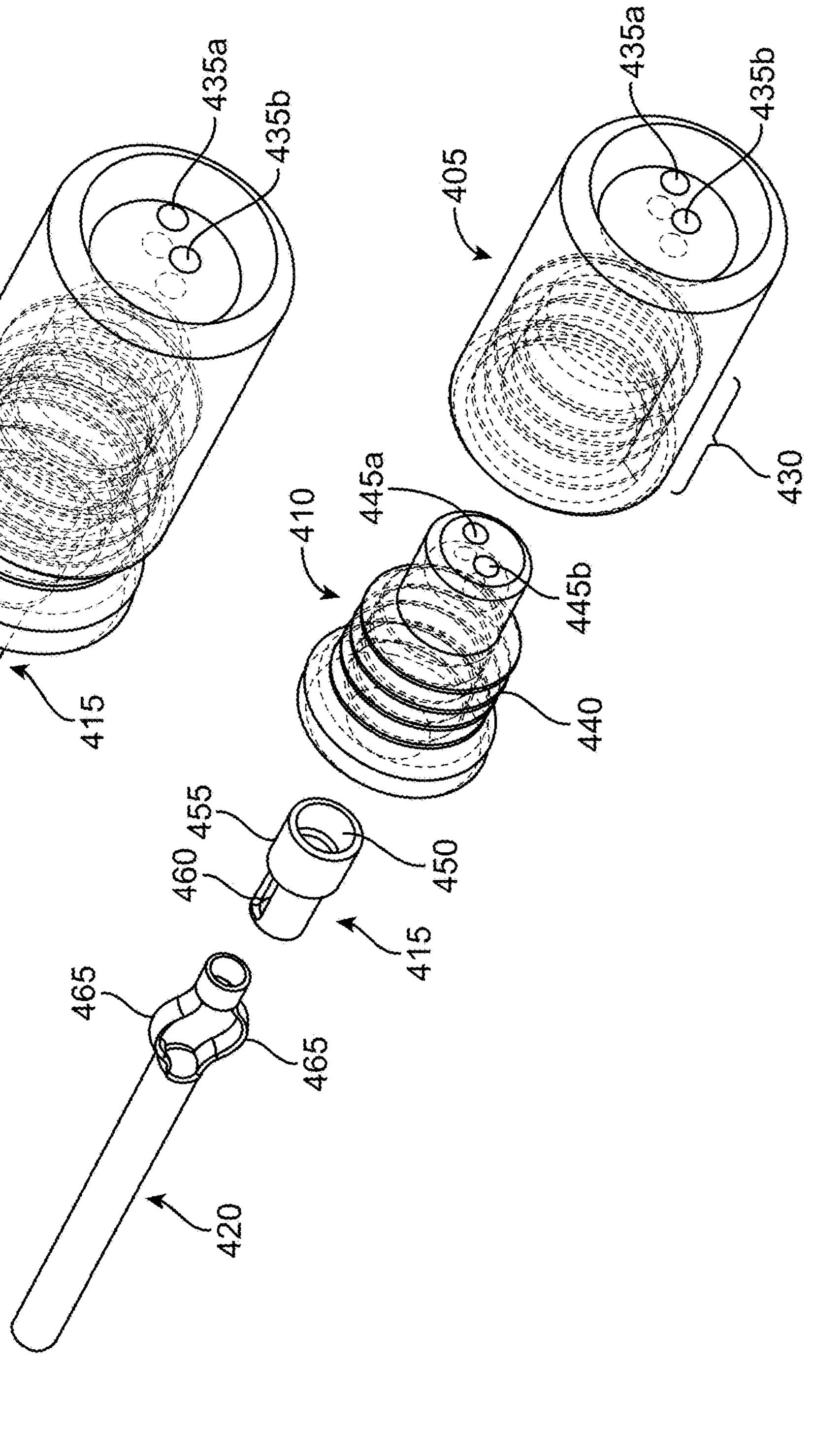

FIG. 18 is a side view of the "knot replacement" tool 400, FIG. 19 is a side exploded view of the "knot replacement" tool 400, FIG. 20 is a perspective view of the "knot replacement" tool 400, and FIG. 21 is a perspective exploded view of the "knot replacement" tool 400.

The "knot replacement" tool 400 includes a locking cap 405, a locking screw 410, a shaft coupler 415 and a delivery shaft 420.

The locking cap 405 is cylindrical in shape with a cylindrical cavity open on a proximal end 405*a* and closed on a distal end 405*b*. The cavity 425 includes an internal threaded portion 430 and the closed end includes first and second tether locking cap holes, 435*a*, 435*b* sized to receive the first and second tethers 305, 315.

The locking screw 410 includes an external threaded portion 440 and a cylindrical cavity that is open on a proximal end 410*a* and closed on a distal end 410*b*. The closed end 410*b* includes first and second tether locking screw holes 445*a*, 445*b* sized to receive the first and second tethers 45*a*, 45*b*. The distal end 410*b* is configured to be inserted into the open proximal end 405*a* of the locking cap 405 and the external threaded portion 440 configured to rotatingly engage with the internal threads 430 so that the locking screw 410 may be screwed into the locking cap 405.

During use, the first and second tethers 305, 315 are inserted through both the first and second tether locking cap holes 435*a*, 435*b* and the first and second tether locking screw holes 445*a*, 445*b*. As the locking screw 410 is rotated in the locking cap 405, the first and second tether locking screw holes, 445*a*, 445*b* are also rotated with respect to the includes first and second tether locking cap holes, 435*a*, 435*b*. During this rotation, the first tether 315 and second tether 315 are twisted around each other and are locked in place.

Connect/Disconnect Feature

The shaft coupler 415 and a delivery shaft 420 are components of a connect/disconnect feature of the "knot replacement" tool 400 that are configured to couple the shaft 415 with the locking screw 410. The coupling of the shaft 420 allows torque to be applied to the locking screw 410. The design also has zero release force when the shaft 420 is uncoupled from the shaft coupler 415. This provides the ability to torque the locking screw 410 and screw the locking screw 410 into the locking cap 405. The shaft 420 can then be uncoupled without disrupting the locking screw 410 and the locking cap 405 when they are locked together.

Figure 22:
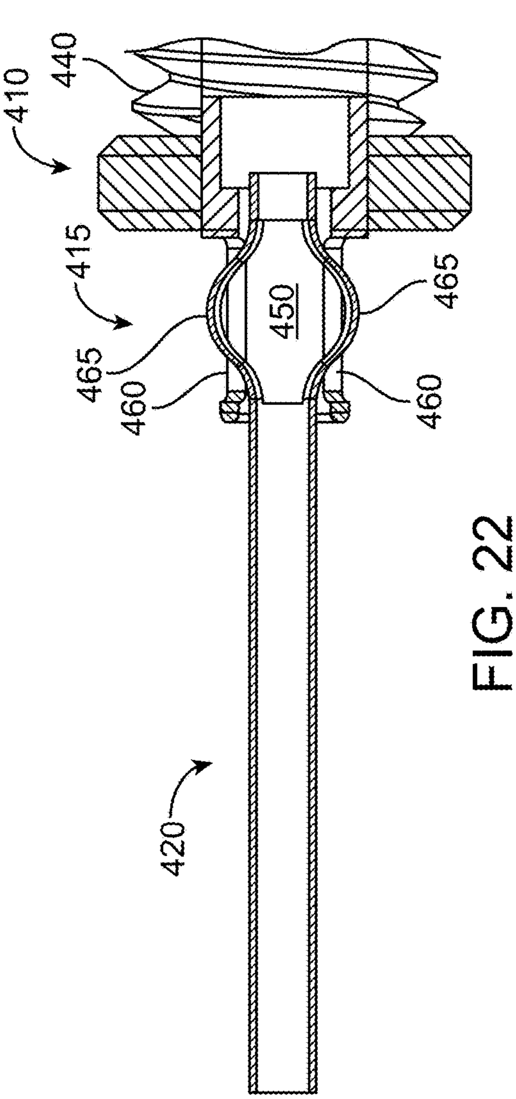
FIGS. 22-23 show components of a connect/disconnect feature of the “knot replacement” tool.

FIG. 22 is a sectional view showing the delivery shaft 420 coupled to the shaft coupler 415. The shaft coupler 415 is cylindrical in shape with a central opening 450 having a proximal portion 455 configured to be inserted into the cylindrical cavity 425 of the locking screw 410 and fixed in place. The shaft coupler 415 also includes slots 460.

The delivery shaft 420 includes a distal end 420*a* with engagement arms 465 having springlike properties that allow them to deflect and spring back to their original position. The distal end 420*a* is configured to be inserted into the into the central opening 450 of the shaft coupler 415.

The distal end of the delivery shaft 420 is sized for insertion into the central opening 450. During insertion, a curved distal portion of the engagement arms 465 contacts the shaft coupler 415 and deflects inwardly into the central opening 450 until the engagement arms 465 line up with the slots 460. Then the spring arms 465 return to their original shape and engage and lock in the slots 460. When the engagement arms 465 are coupled with the slots 460, the locking screw 410 may be rotated or torqued in the locking cap 405.

Figure 23:
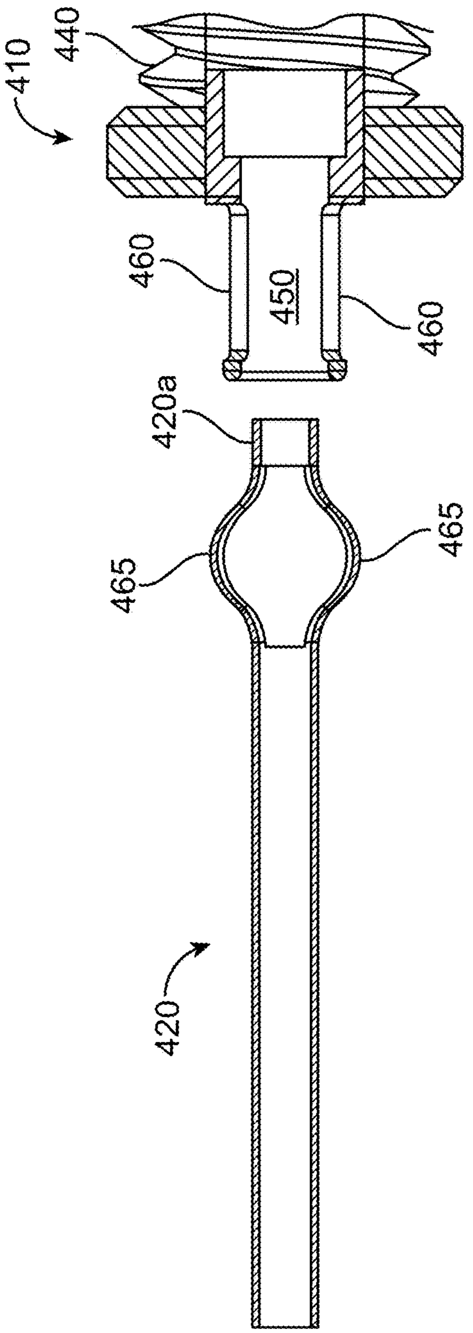

FIG. 23 is a sectional view showing the delivery shaft 420 disengaged from the shaft coupler 415. To disconnect the delivery shaft 420 from the shaft coupler 415, a removal tube is distally slid over the delivery shaft 420 until it engages the proximal end of the shaft coupler 415. Once the removal tool is engaged, the delivery shaft 420 is pulled proximally and the engagement arms 465 deflect inward, allowing removal of the delivery shaft 420 from the central opening of the shaft coupler 415.

Cutter

FIGS. 24-28 are views showing one embodiment of a cutter 500 that is configured to couple with the first and second exposed tethers 305, 315 outside the body. The first and second tethers 305, 315 enter an opening in the distal end and exit from inner and outer side openings 520, 530. The cutter 500 then uses the first and second tethers 305, 315 as a "rail" to guide the cutter 500 to the to the targeted location proximate the "knot replacement" tool 400 at the first and second leaflets 45*a*, 45*b*.

FIG. 24 is a side view and FIG. 25 is a sectional view of a cutter 500, FIG. 26 is a distal perspective view showing more details of the cutting area of the cutter 500, FIG. 27 is a perspective view of the cutter 500, and FIG. 28 is a distal perspective view showing routing of the first and second tethers 305, 315 with the cutter 500.

The cutter 500 includes an outer cutter body 505 coupled to a braided polyimide shaft 510 and a distal stopper 515. The outer cutter body is a cylindrical tube with a side opening 520. An inner cutter body 525 is positioned within the outer cutter body 505. The inner cutter body 525 is a cylindrical tube with a side opening 530. The side openings 520 and 530 of the outer cutter body 505 and the inner cutter body 520 are positioned to provide an opening to a center lumen 555. A proximal stopper 535 which directs the tether ends through the outer and inner cutter bodies aligned side openings 520, 530. It is coupled to the distal end of the inner cutter body 525. A high torque flexible cable or torque shaft 540 is slidably positioned within the lumen of the components. The high torque cable 540 is used to rotate a thread 545 that drives the inner cutter body 525 in an axial direction 550 to scissor cut the tethers 305, 315 between the sharp edges of the inner cutter opening 530 and outer cutter opening 520. The distal end of the flexible cable 540 is positioned proximally of the side openings 520 and 530 during delivery. Once the cutter 500 is in the desired position, the tethers 305, 315 are tensioned, and the flexible cable 540 is rotated to drive the threaded cutter mechanism that moves the inner cutter 525 relative to the outer cutter 505 to cut the first and second tethers 305, 315.

Using the "Knot Replacement" Tool

Figure 29:
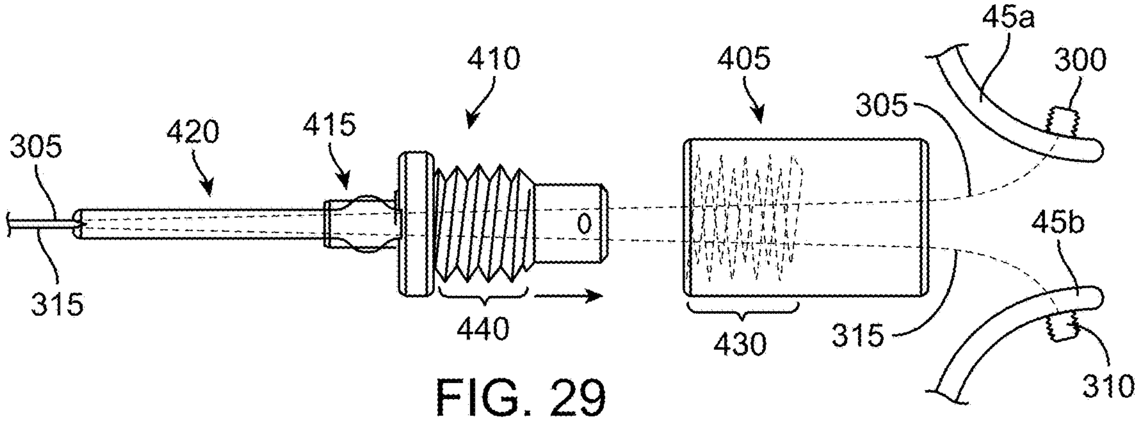
FIGS. 29-31 are views showing the “knot replacement” tool during use.
Figure 30:
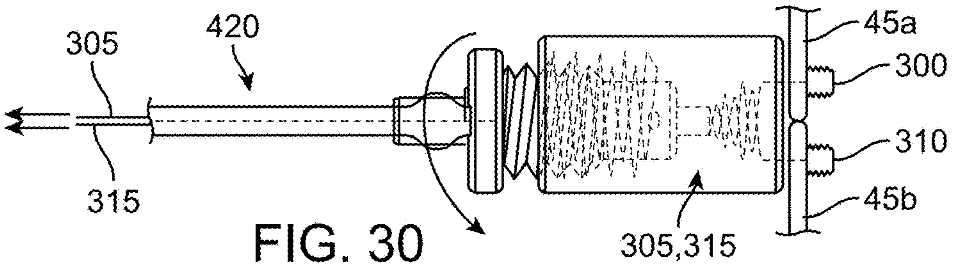
Figure 31:
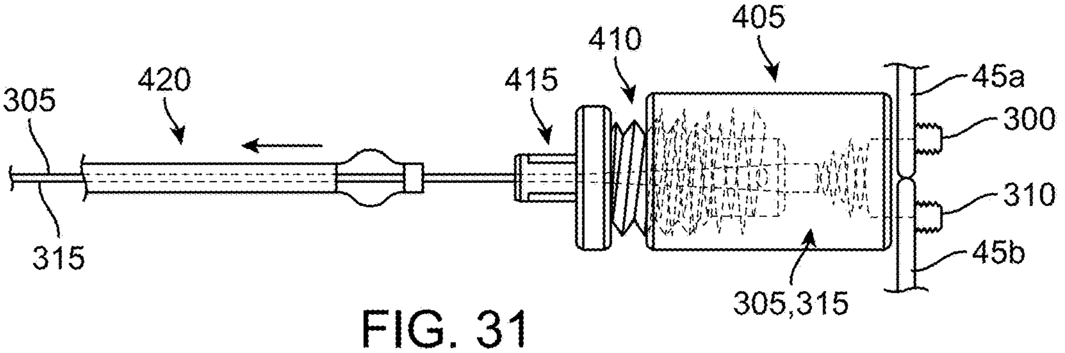

FIGS. 29-31 are views showing the "knot replacement" tool 400 engaging the first and second tethers 305, 315 attached to the first and second leaflets 45*a*, 45*b*, tensioning the first and second tethers 305, 315 to bring the first and second leaflets together 45*a*, 45*b*, and “locking” the first and second tethers 305, 315 in place.

FIG. 29 shows the first and second tethers 305, 315 inserted through the first and second tether locking cap holes, the first and second locking screw holes, through the central opening in the shaft connector and the interior lumen of the deliver shaft. The “knot replacement” tool 400 used the first and second tethers 305, 315 as a “rail” to guide the “knot” replacement tool 400 to the targeted location proximate the mitral valve 45 and first and second leaflets 45*a*, 45*b*.

FIG. 30 shows tensioning of the first and second tethers 305, 315 to pull the first and second leaflets 45*a*, 45*b* together to engage the locking cap 405. The locking screw 410 is then inserted into the locking cap and the delivery shaft 420 rotates the locking screw 410. At the same time, the first tether 305 and second tether 315 are twisted around each other and locked in place.

FIG. 31 shows the delivery shaft 420 being disconnected from the shaft coupler 415 and removed.

Figure 32:
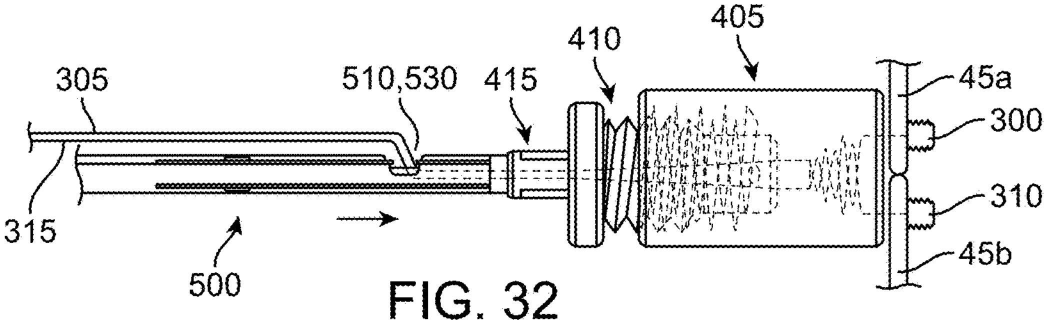
FIG. 32 shows the cutter during use.

FIG. 32 shows a cutter 50 that also uses the first and second tethers 305, 315 as a “rail” to guide to the targeted location proximate the knot” replacement tool 400. The cutter 500 cuts the first and second tethers 305, 315 on the proximal side of the shaft coupler 415. The cutter 500 is then removed along with the cut portions of the first and second tethers 305, 315.

Figure 33:
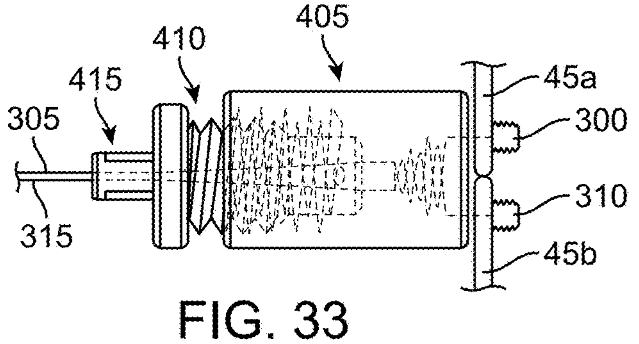
FIG. 33 shows the repaired first and second leaflets.

FIG. 33 shows the repaired first and second leaflets 45*a*, 45*b*.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A system for edge-to-edge repair of a mitral valve comprising:
- an integrated therapy catheter configured to engage a first leaflet and a second leaflet of a mitral valve having:
  - a puncture device configured to:
    - puncture a first hole in the first leaflet; and
    - puncture a second hole in the second leaflet;
  - a delivery device configured to:
    - deliver a first leaflet anchor through the first hole, the first leaflet anchor having a first tether with distal end configured to engage the distal side of the first leaflet; and
    - deliver a second leaflet anchor through the second hole, the second leaflet anchor having a second tether with distal end configured to engage the distal side of the second leaflet; and
- a knot replacement tool configured to tension the first and second tether to bring the first and second leaflet edges together and lock the first and second tethers together, the knot replacement tool includes:
  - a locking cap having a cylindrical cavity with an open proximal end with an internal threaded portion and a closed distal end with first and second tether locking cap holes, the first and second tethers being inserted through the first and second locking cap holes;
  - a locking screw having a cylindrical body with an external threaded portion configured to rotatingly engage with the internal threaded portion of the locking cap, and first and second tether locking screw holes, the first and second tethers being inserted through the first and second locking screw holes; and
- wherein the locking screw is configured to be screwed into the locking cap, with the first and second tether locking screw holes and the first and second tether locking cap holes being rotated in opposite directions so that the first tether and second tether are twisted around each other and are locked in place.

2. The system of claim 1, wherein knot replacement tool further includes a detachable delivery shaft coupled with the locking screw.

3. The system of claim 1, further comprising a cutter device configured to cut the first and second tethers.

4. The system of claim 3, wherein cutter device includes:
- an outer body with an outer body side opening; and
- an inner body with an inner body side opening slidably positioned within the outer body, the inner body side opening and the outer body side opening are positioned to provide an opening to a center lumen,
- wherein the first and second tethers enter a distal end of the center lumen and exit out through the inner body side opening and outer body side opening, and
- axial movement of the inner body in relation to the outer body side opening closes the opening to the center lumen and scissor cuts the first and second tethers.

5. The system of claim 1, wherein the integrated therapy catheter further includes a clamping device configured to clamp a leaflet, the clamping device having a distal clamp portion slidably coupled to a proximal body portion, wherein the distal clamp portion is configured to slide distally to position the leaflet between the distal clamp portion and the proximal body portion and then the distal clamp portion is configured to slide proximally and the leaflet is clamped between the distal clamp portion and the proximal body portion.

6. The system of claim 5, wherein puncture device includes a cannulated needle positioned within the proximal body configured to extend distally to puncture a hole in the leaflet.

7. The system of claim 6, wherein delivery device is configured to deliver a leaflet anchor through the cannulated needle.

8. The system of claim 1, wherein distal ends of the first and second tethers are self-expanding and configured to expand larger than the first and second holes.

9. The system of claim 1, wherein the puncture device configured to puncture the first hole proximate a first leaflet edge and puncture a second hole proximate a second leaflet edge.

10. A system for edge-to-edge repair of a mitral valve comprising:
- an integrated therapy catheter configured to engage a first leaflet and a second leaflet of a mitral valve having:
  - a puncture device configured to puncture a first hole in the first leaflet proximate a first leaflet edge and puncture a second hole in the second leaflet proximate a second leaflet edge;
  - a delivery device configured to:
    - deliver a first leaflet anchor through the first hole to a distal side of the first leaflet, the first leaflet anchor having a first tether with a self-expanding distal end configured to expand larger than the first hole and engage the distal side of the first leaflet; and deliver a second leaflet anchor through the second hole to a distal side of the second leaflet, the second leaflet anchor having a second tether with a self-expanding distal end configured to expand larger than the first hole and engage the distal side of the second leaflet; and a knot replacement tool configured to couple with the first tether and the second tether and tension the first tether and the second tether to bring the first leaflet edge and the second leaflet edge together, and lock the first tether and tether second tether together, the knot replacement tool includes:

a locking cap having a cylindrical body with an internal threaded portion and a closed distal end having a first tether locking cap hole and a second tether locking cap hole, the first and second tethers being inserted through the first and second locking cap holes; and a locking screw having a cylindrical body with an external threaded portion and a closed distal end having first and second tether locking screw holes, the first and second tethers being inserted through the first and second locking screw holes;

wherein the locking screw is configured to be screwed into the locking cap, with the first and second tether locking screw holes and the first and second tether locking cap holes rotated in opposite directions so that the first tether and second tether are twisted around each other and are locked in place.

11. The system of claim 10, wherein the integrated therapy catheter further includes a clamping device configured to clamp a leaflet, the clamping device having a distal clamp portion slidably coupled to a proximal body portion, wherein the distal clamp portion is configured to slide distally to position the leaflet between the distal clamp portion and the proximal body portion and then the distal clamp portion is configured to slide proximally and the leaflet is clamped between the distal clamp portion and the proximal body portion.

12. The system of claim 11, wherein puncture device includes a cannulated needle positioned within the proximal body configured to extend distally to puncture a hole in the leaflet.

13. The system of claim 12, wherein delivery device is configured to deliver a leaflet anchor through the cannulated needle.

14. The system of claim 10, wherein the knot replacement tool further includes a detachable delivery shaft coupled with the locking screw.

15. The system of claim 10, further comprising a cutter device configured to cut the first and second tethers, the cutter device includes:

an outer body that is a cylindrical tube with outer body side opening; and an inner body slidably positioned within the outer body, the inner body is a cylindrical tube with an inner body side opening, the inner body side opening and the outer body side opening are positioned to provide an opening to a center lumen, wherein the first and second tethers enter the distal end of the center lumen and exit out of the center lumen through the inner body side opening and outer body side opening, and axial movement of the inner body scissor cuts the first and second tethers between the edges of the inner body side opening and outer body side opening.

16. A system for edge-to-edge repair of a mitral valve comprising:

an integrated therapy catheter configured to engage a first leaflet and a second leaflet of a mitral valve having:

a puncture device configured to puncture a first hole in the first leaflet proximate a first leaflet edge and puncture a second hole in the second leaflet proximate a second leaflet edge;

a delivery device configured to:

deliver a first leaflet anchor through the first hole to a distal side of the first leaflet, the first leaflet anchor having a first tether with a self-expanding distal end configured to expand larger than the first hole and engage the distal side of the first leaflet; and deliver a second leaflet anchor through the second hole to a distal side of the second leaflet, the second leaflet anchor having a second tether with a self-expanding distal end configured to expand larger than the first hole and engage the distal side of the second leaflet;

a knot replacement tool configured to couple with the first tether and the second tether and tension the first tether and the second tether to bring first leaflet edge and the second leaflet edge together, and lock the first tether and tether second tether together, the knot replacement tool includes:

a locking cap having a cylindrical body with an internal threaded portion and a closed distal end having a first tether locking cap hole and a second tether locking cap hole, the first and second tethers being inserted through the first and second locking cap holes; and a locking screw having a cylindrical body with an external threaded portion and a closed distal end having first and second tether locking screw holes, the first and second tethers being inserted through the first and second locking screw holes;

wherein the locking screw is configured to be screwed into the locking cap, with the first and second tether locking screw holes and the first and second tether locking cap holes rotated in opposite directions so that the first tether and second tether are twisted around each other and are locked in place; and a cutter device configured to cut the first and second tethers.

17. The system of claim 16, wherein the cutter device includes:

an outer body that is a cylindrical tube with outer body side opening; and an inner body slidably positioned within the outer body, the inner body is a cylindrical tube with an inner body side opening, the inner body side opening and the outer body side opening are positioned to provide an opening to a center lumen, wherein the first and second tethers enter the distal end of the center lumen and exit out of the center lumen through the inner body side opening and outer body side opening, and axial movement of the inner body scissor cuts the first and second tethers between the edges of the inner body side opening and outer body side opening.

* * * * *